(12) United States Patent
Sakai et al.

(10) Patent No.: US 9,307,951 B2
(45) Date of Patent: Apr. 12, 2016

(54) ULTRASOUND DIAGNOSIS APPARATUS (75) Inventors: Ryoichi Sakai, Mitaka (JP); Akimitsu Harada, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 569 days.

(21) Appl. No.: 11/835,819

(22) Filed: Aug. 8, 2007

(65) Prior Publication Data

US 2009/0043196 A1 Feb. 12, 2009

(51) Int. Cl.
*A61B 8/00* (2006.01)
*A61B 8/08* (2006.01)

(52) U.S. Cl.
CPC ............... *A61B 8/0875* (2013.01); *A61B 8/485* (2013.01)

(58) Field of Classification Search
None
See application file for complete search history.

(56) References Cited

U.S. PATENT DOCUMENTS

| 5,493,788 | A | 2/1996 | Richardson | |
|---|---|---|---|---|
| 5,558,091 | A | 9/1996 | Acker et al. | |
| 5,588,435 | A | 12/1996 | Weng et al. | |
| 5,953,073 | A * | 9/1999 | Kozina et al. | 348/558 |
| 6,569,098 | B2 | 5/2003 | Kawchuk | |
| 2003/0125623 | A1* | 7/2003 | Kelly et al. | 600/437 |
| 2003/0125625 | A1* | 7/2003 | Kelly et al. | 600/443 |
| 2003/0125626 | A1* | 7/2003 | Kelly et al. | 600/443 |
| 2004/0015079 | A1* | 1/2004 | Berger et al. | 600/437 |
| 2004/0015080 | A1* | 1/2004 | Kelly et al. | 600/437 |
| 2005/0148860 | A1 | 7/2005 | Liew et al. | |
| 2005/0273009 | A1* | 12/2005 | Deischinger et al. | 600/437 |
| 2006/0020202 | A1* | 1/2006 | Mathew et al. | 600/437 |
| 2006/0036173 | A1* | 2/2006 | Kelly et al. | 600/443 |
| 2006/0074311 | A1* | 4/2006 | Sakai et al. | 600/437 |
| 2006/0241447 | A1* | 10/2006 | Harada et al. | 600/443 |
| 2007/0060798 | A1* | 3/2007 | Krupnik et al. | 600/300 |
| 2007/0073149 | A1* | 3/2007 | Kelly et al. | 600/437 |
| 2008/0086055 | A1* | 4/2008 | Sakai et al. | 600/438 |
| 2009/0043207 | A1* | 2/2009 | Sakai | 600/449 |
| 2009/0171200 | A1* | 7/2009 | Sakai | 600/438 |

FOREIGN PATENT DOCUMENTS

| EP | 1523940 A1 | 4/2005 |
|---|---|---|
| EP | 1707124 A2 | 1/2006 |
| EP | 1693004 A1 | 8/2006 |

(Continued)

OTHER PUBLICATIONS

European Search Report dated Feb. 4, 2008, issued in corresponding European Patent Application No. 07019540.9.

(Continued)

*Primary Examiner* — Michael Rozanski
(74) *Attorney, Agent, or Firm* — Westerman, Hattori, Daniels & Adrian, LLP (57) ABSTRACT

A flexure display is a display graph in which positions of a plurality of surface points and amounts of displacement are correlated. A slider provides a user interface for setting time. A time which is set through the slider is reflected on the flexure display or the like. The flexure display provides a graph showing an amount of displacement of each surface point at the time which is set through the slider. A load display shows a temporal change of an amount of load applied to the bone. A strain display shows a temporal change of an amount of strain of the bone. Time markers showing a predetermined time are displayed on the load display and strain display. The time markers are displayed according to the time which is set through the slider.

15 Claims, 7 Drawing Sheets

(56) References Cited

FOREIGN PATENT DOCUMENTS

| | | | |
|---|---|---|---|
| JP | 7-222742 | A | 8/1995 |
| JP | 9-503410 | A | 4/1997 |
| JP | 10-503671 | A | 4/1998 |
| JP | 2001-231788 | A | 8/2001 |
| JP | 2001309918 | A | 11/2001 |
| JP | 2002-34986 | A | 2/2002 |
| JP | 2004-157815 | A | 6/2004 |
| JP | 2004298205 | A | 10/2004 |
| JP | 2005-102945 | A | 4/2005 |
| JP | 2005-152079 | A | 6/2005 |
| WO | 95/35062 | A2 | 12/1995 |

OTHER PUBLICATIONS

Japanese Office Action dated Sep. 30, 2008 (mailed date), issued in corresponding Japanese Application No. 2006-276121.
Japanese Office Action dated Jul. 13, 2010, issued in corresponding Japanese Patent Application No. 2006-117541.
Office Action dated Oct. 18, 2010, issued in U.S. Appl. No. 11/869,238.
Notice of Allowance dated Oct. 31, 2011, issued in related U.S. Appl. No. 11/869,238.
Office Action dated Apr. 14, 2011, issued in corresponding U.S. Appl. No. 11/869,238.

* cited by examiner

ULTRASOUND DIAGNOSIS APPARATUS

BACKGROUND

1. Technical Field

The present invention relates to a technique for displaying a measurement result of a shape of a bone which is measured using an ultrasound.

2. Description of the Related Art

Simple quantitative measurement of mechanical characteristics such as bone strength is desired for diagnosing bone metabolic diseases such as osteoporosis, judging fracture risk, and quantitatively diagnosing bone union after treatment of bone fracture.

The evaluation of bone formation and bone union depends largely on X-ray photography, but quantitatively diagnosing bone strength by means of X-ray photography is complex and difficult. One known method of measuring bone strength in the related art is a physical strength test of a sample of the measurement target. However, this method requires an extraction operation for obtaining a sample bone, and thus, the method is invasive. A method of measuring an amount of bone and a bone density has employed devices such as X-ray CT and DXA (dual-energy X-ray absorptiometry). However, these devices are merely means for measuring the amount of bone and cannot provide an evaluation of bone strength. Moreover, in view that tissue is irradiated with X-rays in these methods, these methods cannot be considered non-invasive.

Other attempts to quantitatively evaluate bone strength include a strain gauge method in which a strain gauge is mounted on an external fixator and the strain of the external fixator is measured; a vibration wave method in which a vibration is applied to a bone from the outside and a characteristic frequency is evaluated: and an acoustic emission method in which acoustic waves generated by a bone which has reached yield stress are detected. These methods, however, have various problems in that a limitation is imposed on the treatment to which these methods can be applied, that the bone is subjected to invasion, and that evaluation precision is insufficient.

In view of the above circumstances, the inventors of the present application have proposed an ultrasound diagnosis apparatus for noninvasively and quantitatively evaluating the mechanical characteristics of bone (JP 2004-298205 A). The ultrasound diagnosis apparatus described in JP 2004-298205 A forms a plurality of ultrasonic beams on a bone, obtains a plurality of echo signals corresponding to the individual ultrasonic beams to specify a surface point corresponding to the bone surface for each echo signal, and generates shape data of the bone surface on the basis of the plurality of surface points obtained from the plurality of echo signals. Then, a mechanical characteristic of the bone is evaluated on the basis of a change in the shape data when an external load is applied to the bone. Thus, the apparatus is an epoch-making technology capable of noninvasively and quantitatively evaluating the mechanical characteristics of a bone in a living organism from the shape data of the bone surface on the basis of the echo signals.

The inventors of the present application have further studied display techniques of the measurement result obtained using the epoch-making technology described in JP 2004-298205 A.

SUMMARY

The present invention was conceived in view of the above-described circumstances, and an advantage of the present invention is that a technique is provided which can display, in an easily understandable manner, a measurement result of a shape of a bone which is measured using an ultrasound.

According to one aspect of the present invention, there is provided an ultrasound diagnosis apparatus comprising a transmission and reception unit which forms a plurality of ultrasonic beams on a bone, a surface detector unit which detects a surface point corresponding to a surface of the bone for each ultrasonic beam, to detect a plurality of surface points based on the plurality of ultrasonic beams, a shape measurement unit which determines a measured quantity reflecting a shape of a bone surface based on the plurality of detected surface points, and an image formation unit which forms a measurement result image in which the measured quantity, an amount of load, and time when a load is applied on the bone are correlated to each other.

DETAILED DESCRIPTION

A preferred embodiment of the present invention will now be described.

Figure 1:
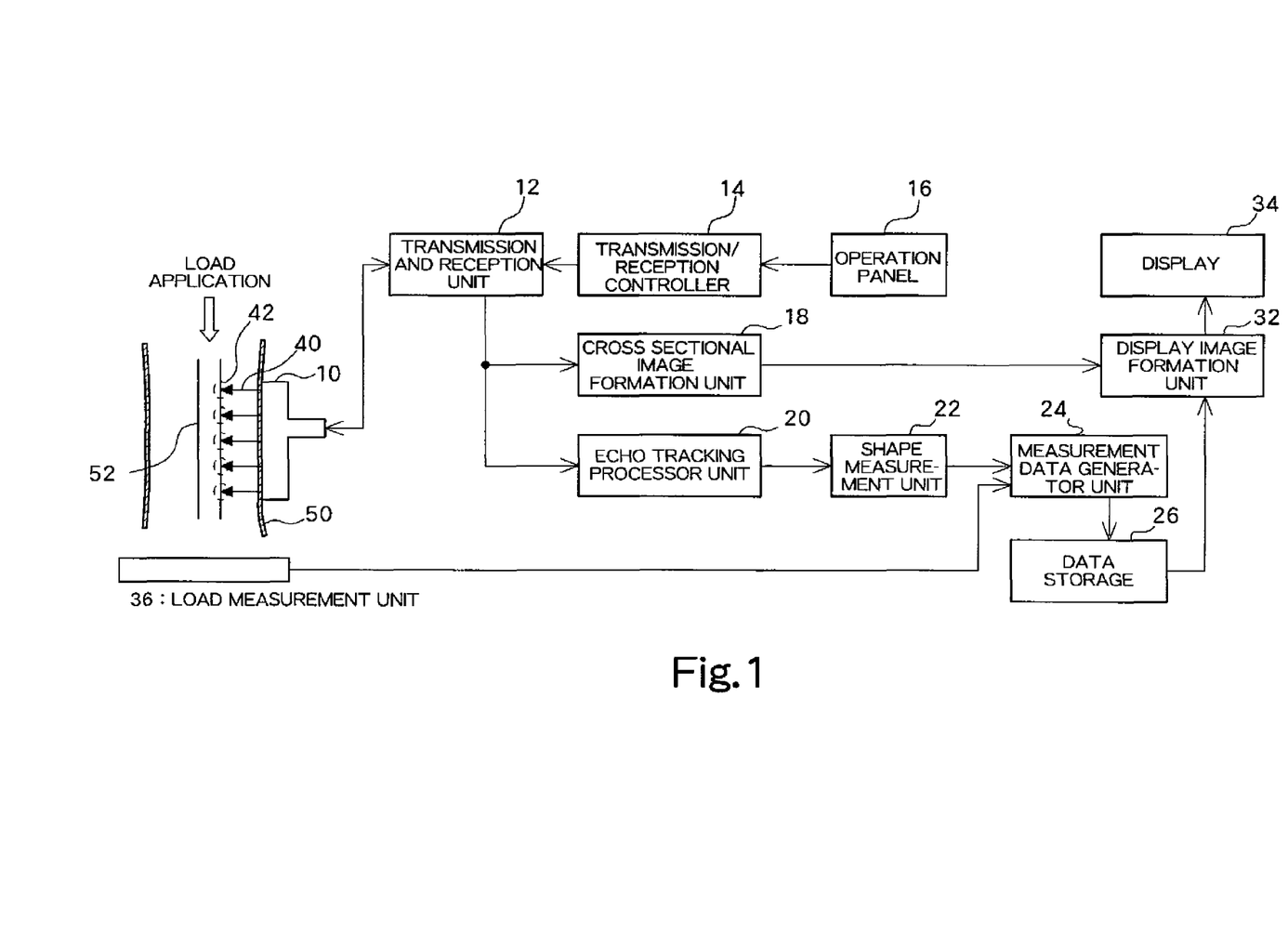
FIG. 1 is a block diagram showing an overall structure of an ultrasound diagnosis apparatus according to a preferred embodiment of the present invention.

FIG. 1 shows a preferred embodiment of an ultrasound diagnostic apparatus according to the present invention. FIG. 1 is a block diagram showing an overall structure of the ultrasound diagnostic apparatus. A probe 10 is an ultrasonic probe which is used in contact with a surface of the body of a subject 50. Alternatively, an ultrasonic probe which is inserted into the subject may be used. The probe 10 directs ultrasound in the form of ultrasonic beams 40 towards a bone 52 within the body of the subject 50. As the probe 10, it is desirable to use a linear electronic scan probe (linear probe) which electronically scans the ultrasonic beam 40. Alternatively, the probe 10 may be a probe which uses a method such as a sector electronic scanning. The bone to be diagnosed may be, for example, a tibia or a fibula. Tracking points 42 which are set on the bone 52 will be described later in more detail.

A transmission and reception unit 12 controls the probe 10 and electronically scans the ultrasonic beam 40 on a cross sectional surface (a cut surface of a subject 50 in FIG. 1). When the probe 10 is a linear probe, for example, sequential electronic scanning of 120 ultrasonic beams 40 (FIG. 1 only shows 5 ultrasonic beams for echo tracking which will be described later) is applied and an echo signal is obtained for each ultrasonic beam 40. The plurality of obtained echo signals are output to a cross sectional image formation unit 18 and the cross sectional image formation unit 18 forms a cross sectional image (B mode image) of the bone 52 based on the plurality of echo signals.

The echo signal obtained in the transmission and reception unit 12 is also output to an echo tracking processor unit 20.

The echo tracking processor unit 20 applies an echo tracking process in which the bone surface section is extracted from each echo signal and is tracked. For the echo tracking process, a technique detailed in JP2001-309918A may, for example, be used. For the echo tracking process, for example, 5 tracking echo signals are used. The tracking echo signals may be selected from among the echo signals used for forming a cross sectional image (for example, 120 echo signals) or may alternatively be obtained by forming 5 tracking echo signals separately from the beams for forming the cross sectional image.

The 5 ultrasonic beams 40 shown in FIG. 1 are beams for obtaining tracking echo signals. An examiner inputs an instruction related to transmission/reception of the ultrasound through an operation panel 16 to a transmission/reception control unit 14 and the transmission/reception control unit 14 controls the transmission and reception unit 12 based on the instruction from the examiner. With this structure, ultrasonic beams 40 for obtaining tracking echo signals are transmitted to a diagnosis site on the bone surface according to the instruction from the examiner. In the transmission/reception of ultrasound, a strong reflected wave is obtained from the bone surface. Therefore, the echo signals obtained from within the body of the diagnosis target (subject) are obtained as having large amplitude in a portion corresponding to bone surface.

In the echo tracking process, a zero-cross point is detected as a representative point of each echo signal, and the extraction precision is significantly increased by tracking the detected zero-cross point. The zero-cross point is detected as a timing within a tracking gate period in which the polarity of the amplitude of the echo signal is inverted from positive to negative or from negative to positive. When a zero-cross point is detected, a new tracking gate which is centered at the zero-cross point is set. Then, for the echo signal obtained from the same site at the next time, a zero-cross point is detected within the newly set tracking gate period. In this manner, for each echo signal, that is, for each ultrasonic beam 40, a zero-cross point is tracked as a surface point. The surface point tracked for each ultrasonic beam 40 is referred to as a tracking point 42.

A shape measurement unit 22 calculates a measured quantity reflecting a shape of a bone surface based on the plurality of detected surface points (tracking points 42). The shape measurement unit 22 measures, as the measured quantity, an amount of displacement of each surface point before and after a load when a load is applied to the bone 52. In other words, the shape measurement unit 22 measures a displacement of the surface point before and after the load from each of the 5 ultrasonic beams 40. As a result, displacements for 5 points on the bone surface are obtained. Although an example configuration with 5 echo tracking echo signals is shown in FIG. 1, the present embodiment is not limited to such a configuration, and a plurality of echo tracking echo signals with a number being other than 5 may be employed for the measurement. In addition, the shape measurement unit 22 measures, as the measured quantity, an amount of strain of a bone when a load is applied to the bone 52.

The load to the bone 52 is realized by any of a number of methods such as, for example, a three-point loading method in which two points on the bone 52 distanced from each other along the axial direction are set as pivots and a load is applied between the two points and a footstep method in which a subject is made to walk so that a load is applied to the bone 52. Alternatively, it is also possible to make the subject hold a weight or the like so that a load is applied to the bone 52 by the weight.

Figure 2:
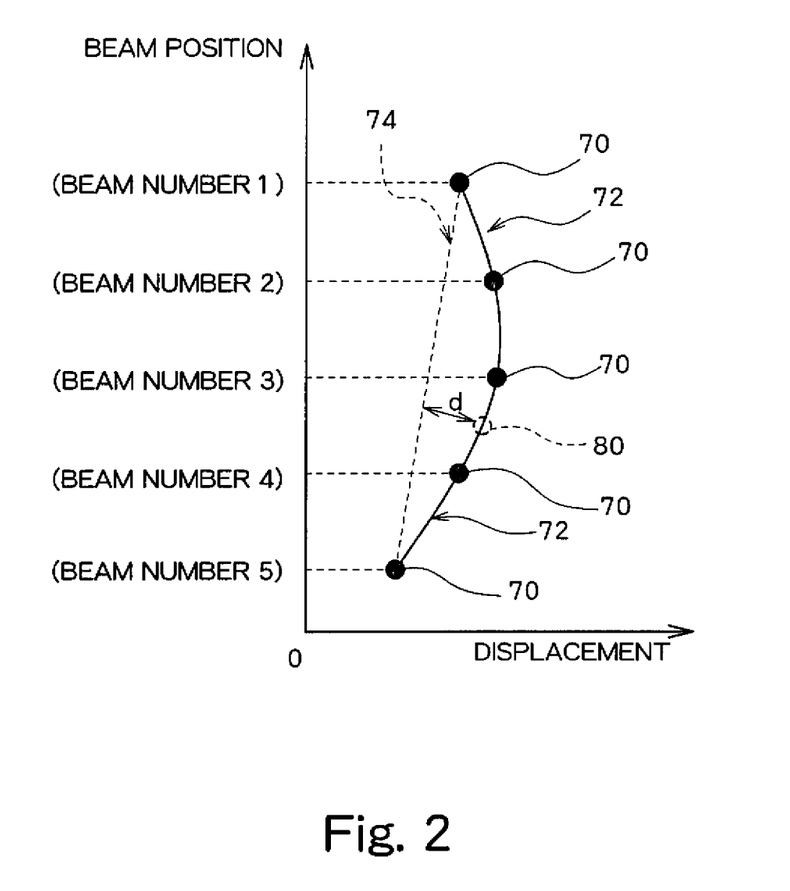
FIG. 2 is a diagram for explaining an amount of displacement and an amount of strain in a bone.

FIG. 2 is a diagram for explaining an amount of displacement and an amount of strain of a bone. FIG. 2 shows a coordinate system in which the beam position of the ultrasonic beam 40 is set on the vertical axis and a displacement of a surface point is set on the horizontal axis. Five actual measurement points 70 are determined as points at which beam positions of the ultrasonic beams and the displacements measured with the ultrasonic beams are correlated. The beam position is a position of each echo tracking ultrasonic beam (height of each ultrasonic beam 40 in FIG. 1) and the beam positions are identified with beam numbers 1-5 in the order from the top (from the higher position).

In order to calculate an amount of strain, an interpolation line 72 is generated connecting the 5 actual measurement points 70. The interpolation line 72 can be obtained, for example, by interpolating a curve for the 5 actual measurement points 70 using, for example, a spline interpolation or a least square interpolation. Further, a degree of curvature of the interpolation line 72 is evaluated based on a comparison of the interpolation line 72 and a line 74 connecting two end points of the 5 actual measurement points 70. More specifically, a distance d between the line 74 and a maximum displacement point 80 which is a point on the interpolation line 72 existing at a point furthest away from the line 74 is calculated, for example, and an amount of strain $\epsilon = d/L$ is calculated as an indicating value indicating an amount of elasticity of the bone based on the length L of the line 74 and the distance d. The amount of strain $\epsilon$ may also be simply referred to as "strain".

The calculation method of the amount of strain is not limited to the method described above with reference to FIG. 2. For example, it is also possible to calculate a distance d as a displacement difference between a displacement at a maximum point among the 5 actual measurement points in which the displacement is maximum and a displacement at a minimum point among the 5 actual measurement points in which the displacement is minimum, and calculate an amount of strain $\epsilon = d/L$ based on that distance d.

With reference again to FIG. 1, a measurement data generator unit 24 generates measurement data in which a measured quantity, an amount of load, and time when a load is applied to the bone are correlated to each other, and stores the measurement data in a data storage 26. An amount of displacement and an amount of strain of the bone of each surface point are supplied to the measurement data generator unit 24 by the shape measurement unit 22. In addition, a measurement result of a load value involved in the application of the load on the bone 52 is supplied from a load measurement device 36 to the measurement data generator unit 24. The measurement data generator unit 24 generates measurement data by correlating, for each surface point, the amount of displacement or the amount of strain of the bone with the load value, and further correlating the time when the load is applied. The time is identified using time information which is obtained from a controller or the like (not shown).

Figure 3:
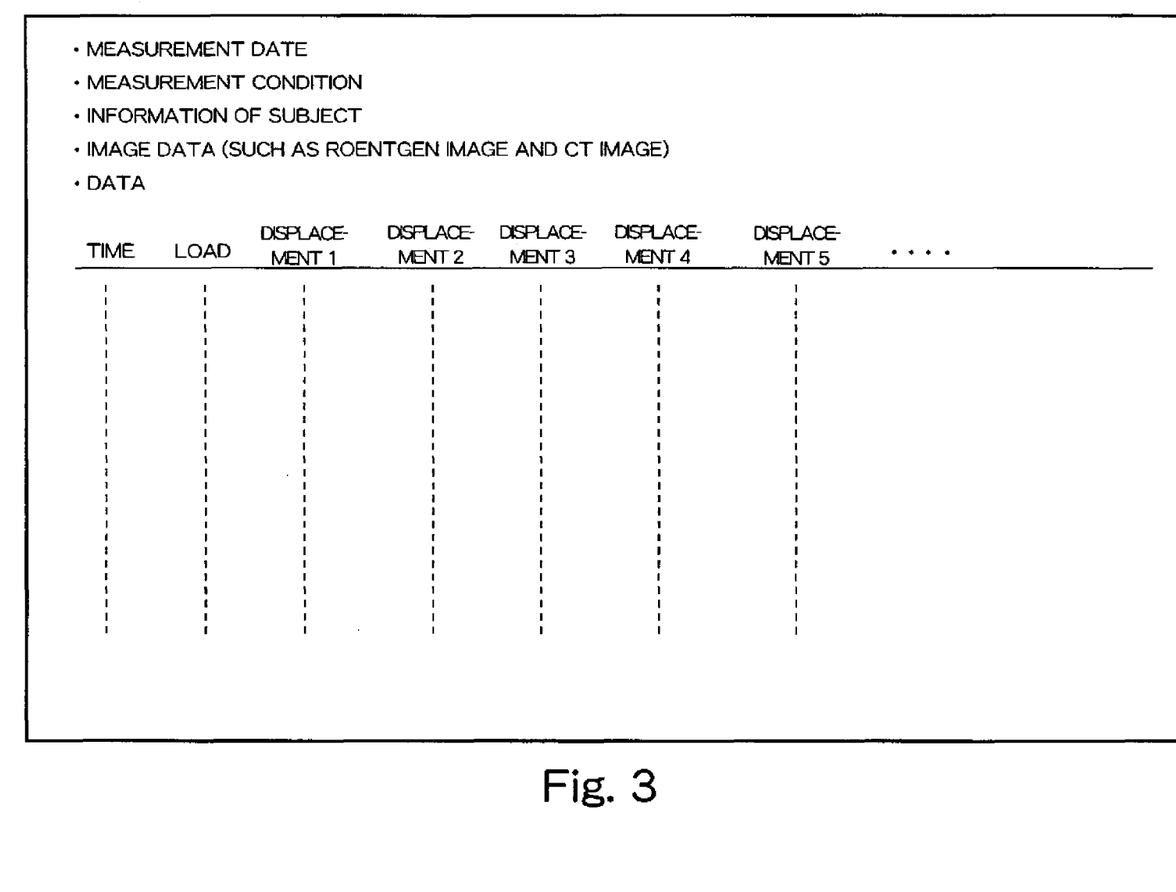
FIG. 3 is a diagram for explaining measurement data.

FIG. 3 is a diagram for explaining the measurement data generated by the measurement data generator unit and stored in the data storage. The measurement data includes information on measurement time when the data is measured (including year, month, and day), a measurement condition, information on subject, etc. In addition, image data or the like of the bone which is the measurement target may be attached. The image data is preferably, for example, a cross sectional image formed by the cross sectional image formation unit 18. Alternatively, it is also possible to attach data of a roentgen image and a CT image as the image data. Moreover, the image data itself may be attached to the measurement data or an address of storage location or the like of the image data may be attached as link information.

A time when the load is applied (time), the load value at that time (load), and the amount of displacement at the surface points (displacements 1-5) are arranged in one horizontal line in correspondence to each other. The displacements 1-5 correspond to displacements obtained based on the beams of the beam numbers 1-5 (refer to FIG. 2), respectively. It is also possible to correlate the amount of strain after the value of the displacement 5. In this manner, the time, load, displacement, etc. are arranged in a horizontal line in correspondence to each other, and data for times different from each other are arranged vertically.

With reference again to FIG. 1, a display image formation unit 32 forms a measurement result image in which the measured quantity, amount of load, ant time are correlated to each other, based on measurement data stored in the data storage 26. The display image formation unit 32 switches between the cross sectional image formed by the cross sectional image formation unit 18 and the measurement result image or forms a display image in which the cross sectional image and the measurement result image are placed side by side. The formed display image is displayed on a display 34.

A characteristic of the ultrasound diagnosis apparatus of the present embodiment is the measurement result image formed by the display image formation unit 32. The measurement result image formed in the present embodiment will now be described with reference to FIGS. 4-7.

Figure 4:
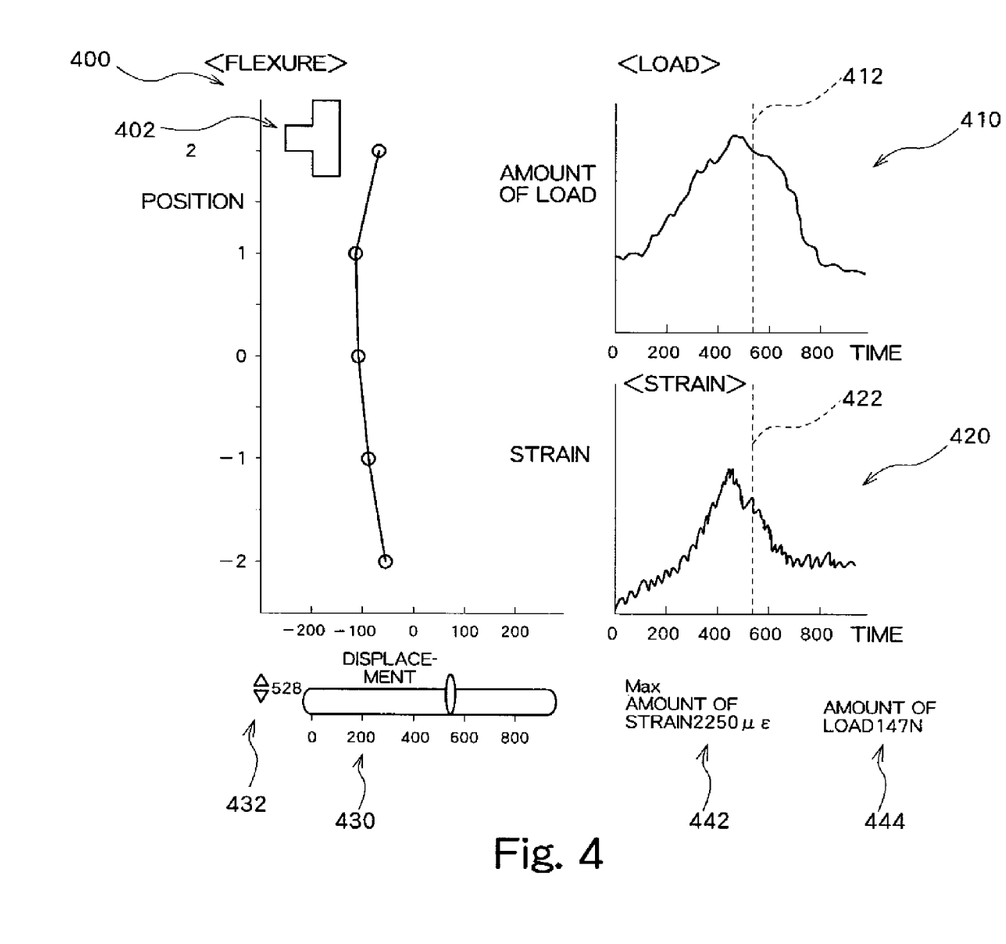
FIG. 4 is a diagram for explaining a first display example of a measurement result image.

FIG. 4 is a diagram for explaining a first example display of a measurement result image. The example display of FIG. 4 includes a flexure display 400 which functions as a displacement graph, a load display 410 which functions as a load graph, a strain display 420 which functions as a strain graph, and a slider 430 which functions as a time setting bar.

The flexure display 400 is a graphical display in which positions of a plurality of surface points and the amounts of displacement are correlated to each other by showing an amount of displacement on each surface point on one axis and a position of each surface point on the other axis. In other words, the flexure display 400 is a graph which shows positions of 5 surface points identified by the beams of beam numbers 1-5 on the vertical axis and the displacements measured by the beams on the horizontal axis. The flexure display 400 corresponds to a display showing a correlation relationship between the displacement and the beam position shown in FIG. 2.

An interpolation line connecting the 5 measurement points (actual measurement points 70 in FIG. 2) shown in the flexure display 400 is displayed. The interpolation line can be obtained by interpolating a curve for the 5 measurement points using a method such as a spline interpolation or a least square interpolation. In this manner, measurement points are connected by the interpolation line so that the degree of the flexure of the bone surface is visually shown.

A probe marker 402 indicating an orientation of the probe is displayed on the flexure display 400. In FIG. 4, the probe marker 402 indicates that the probe is placed at an orientation to transmit an ultrasonic beam towards right of the figure (a direction of increasing displacement). In addition, it is also possible to attach a numerical value display for, for example, a maximum value and a minimum value of the amount of displacement, an amount of strain of the bone, etc. in the flexure display 400.

The slider 430 provides a user interface for setting a time. Specifically, an examiner (user) sets the marking of the slider 430 to a desired time by operating on the slider 430 using a mouse or a keyboard. An adjustment button 432 for finely adjusting the time is displayed near the slider 430. The examiner can set an approximate time using the slider 430 and then finely adjust the time using the adjustment button 432.

The time which is set through the slider 430 and the adjustment button 432 are reflected in the flexure display 400, etc. In other words, the flexure display 400 provides a graph showing the amounts of displacements at the surface points at the time which is set through the slider 430 or the like.

The load display 410 is a graph in which the time and the amount of load are correlated to each other by showing the time on one axis and the amount of load on the other axis. In other words, the load display 410 shows a temporal change of the amount of load (load value) applied to the bone. A time marker 412 showing a predetermined time is displayed on the load display 410. The time marker 412 is shown according to the time which is set through the slider 430 or the like. In other words, when the time is changed using the slider 430, for example, the time marker 412 in the load display 410 slides along the time axis direction according to the time changing operation (sliding operation) on the slider 430.

Because of this, the examiner is able read, from the load display 410, the load value at the set time through the time marker 412. In addition, the load value at the time corresponding to the time marker 412 may be numerically displayed on the load display 410.

The strain display 420 is a graph in which the time and the amount of strain are correlated to each other by showing the time on one axis and the amount of strain on the other axis. In other words, the strain display 420 shows a temporal change of the amount of strain $\epsilon=d/L$ (refer to FIG. 2). A time marker 422 which shows a predetermined time is displayed on the strain display 420. The time marker 422 is displayed according to the time which is set through the slider 430 or the like. In other words, similar to the time marker 412 in the load display 410, the time marker 422 in the strain display 420 slides along the time axis direction according to a time changing operation on the slider 430.

Because of this, the examiner is able to read, from the strain display 420, the amount of strain at the set time through the time marker 422. In addition, the amount of strain at the time corresponding to the time marker 422 may be numerically displayed.

As described, in the display example of FIG. 4, a display form is provided in which the measured quantity (amount of displacement or amount of strain), amount of load (load value), and time when a load is applied to the bone are correlated to each other. More specifically, according to the time which is set through the slider 430 and the adjustment button 432, an amount of displacement at that time is displayed on the flexure display 400, the load value at that time can be read from the load display 410, and the amount of strain at that time can be read from the strain display 420.

Alternatively, it is also possible to numerically display a maximum value 442 of the amount of strain and a maximum value 444 of the amount of load within the measurement period. In addition, the display positions of the flexure display 400, load display 410, and strain display 420 can be moved according to an operation of the examiner or the like. Moreover, the flexure display 400, the load display 410, and the strain display 420 need not be displayed simultaneously. Furthermore, it is also possible to form a display screen in which the display of FIG. 4 is combined with other display forms described with reference to FIGS. 5-7.

Figure 5:
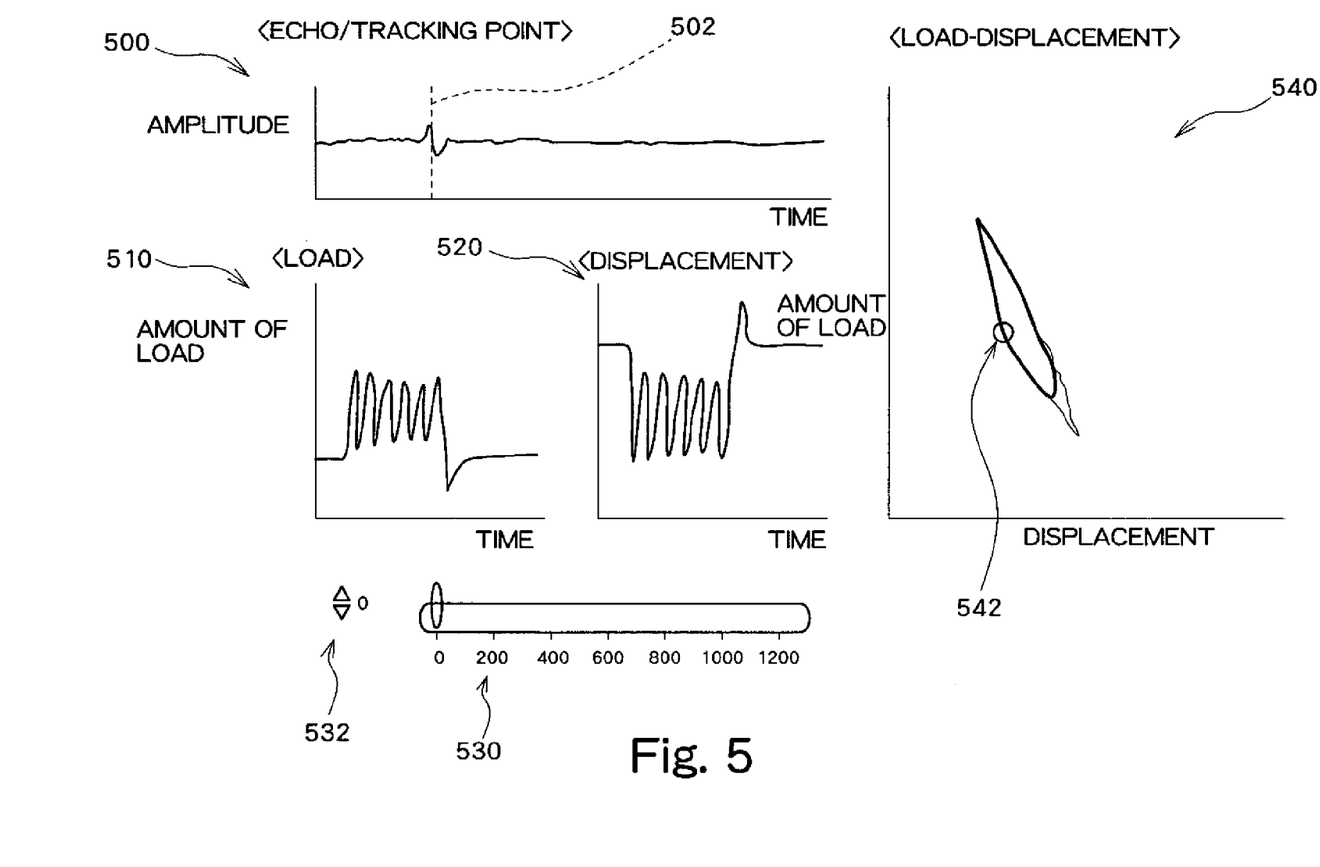
FIG. 5 is a diagram for explaining a second display example of a measurement result image.

FIG. 5 is a diagram for explaining a second display example of the measurement result image. The display example shown in FIG. 5 includes an echo/tracking point display 500, a load display 510, a displacement display 520, a load-displacement display 540 which functions as a characteristic curve graph, and a slider 530 which functions as a time setting bar.

The echo/tracking point display 500 displays an echo waveform by showing a time on the horizontal axis and an amplitude of the echo on the vertical axis. The echo/tracking point display 500 displays, for example, an echo waveform of a beam number selected by the operator. In addition, a tracking point marker 502 is displayed on the echo/tracking point display 500. The tracking point marker 502 is a marker which indicates a tracking point in the echo waveform.

The operator can visually check the state of the echo waveform and the tracking state of the tracking point based on the echo/tracking point display 500. It is also possible to employ a configuration in which the operator sets an initial position of the tracking gate using the echo/tracking point display 500.

The load display 510 shows the change over a period of time of the amount of load (load value) applied to the bone. The display example of FIG. 5 is suited for measurement by a load which is periodically and repeatedly applied. For example, the display example of FIG. 5 is used for measurement using a load which shows a temporal change having a shape similar to a sine wave. The displacement display 520 shows a temporal change of the amount of displacement of the surface point. For example, the amount of displacement measured by the ultrasonic beam of the beam number selected by the operator is displayed. The amount of displacement shows a periodical temporal change corresponding to the temporal change of the load which is applied periodically and repeatedly.

The slider 530 provides a user interface for setting time. That is, the examiner sets the marking of the slider 530 to a desired time by operating the slider 530 using a mouse, a keyboard, etc. An adjustment button 532 for finely adjusting time is displayed near the slider 530. The examiner can set an approximate time using the slider 530 and then finely adjust the time using the adjustment button 532.

The load-displacement display 540 is a graph showing the measured quantity on one axis and the amount of load on the other axis. In other words, the load-displacement display 540 is a graph which directly represents a correspondence relationship between the load and the displacement by showing the amount of displacement which is the measured quantity on the horizontal axis and the load value on the vertical axis. The load-displacement display 540 shows a correspondence relationship between a periodic load displayed on the load display 510 and the periodic displacement displayed on the displacement display 520 obtained corresponding to the load.

The curve displayed on the load-displacement display 540 forms a hysteresis loop. This occurs due to the fact that the bone has a viscous characteristic in addition to the elastic characteristic. That is, because the displacement follows the periodic load with a delay, the curve displayed on the load-displacement display 540 forms a loop. Therefore, the curve displayed on the load-displacement display 540 is one of preferable displays for evaluating a viscoelasticity or the like of the bone.

A time marker 542 which indicates a predetermined time is displayed on the load-displacement display 540. The time marker 542 is displayed according to a time which is set through the slider 530 or the like. More specifically, when time is changed using the slider 530 or the like, the time marker 542 in the load-displacement display 540 moves along the curve according to a time changing operation (sliding operation) in the slider 530.

As described, the load-displacement display 540 shown in FIG. 5 provides a display form in which the measured quantity (amount of displacement), amount of load (load value), and time when a load is applied to the bone are correlated directly to each other. It is also possible to form a graph which directly represents a correspondence relationship between the load and the amount of strain by showing the amount of strain on the horizontal axis and the load value on the vertical axis.

The echo/tracking point display 500, the load display 510, the displacement display 520, and the load-displacement display 540 need not be displayed simultaneously. In addition, it is also possible to form a display screen in which the display of FIG. 5 is combined with the other display forms described with reference to FIGS. 4, 6, and 7.

Figure 6:
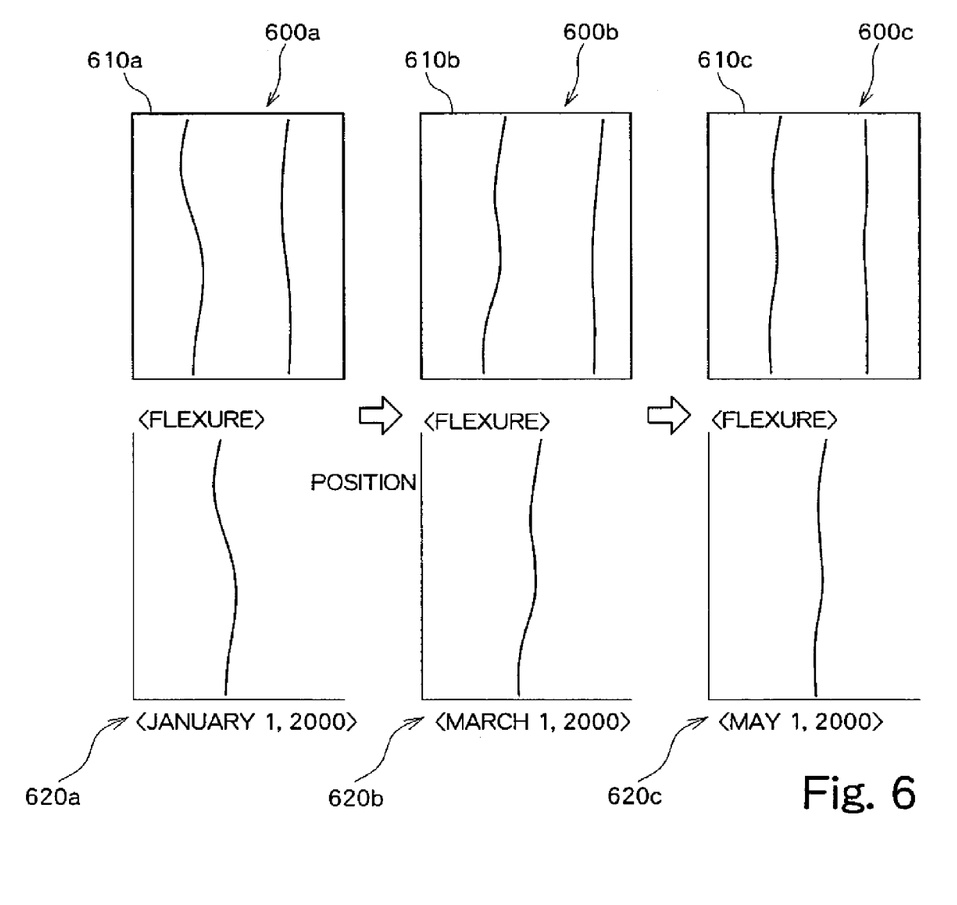
FIG. 6 is a diagram for explaining a third display example of a measurement result image.

FIG. 6 is a diagram for explaining a third display example of a measurement result image. The display example shown in FIG. 6 is a display example showing a state of temporal change of the shape of the bone surface based on a plurality of displacement graphs obtained at timings which differ from each other. More specifically, the display example of FIG. 6 includes flexure displays (620a, 620b, and 620c) which function as displacement graphs and images of the bone (610a, 610b, and 610c) at the timings when the flexure displays are obtained.

Each flexure display is a display graph in which positions of a plurality of surface points and amounts of displacement are correlated by showing an amount of displacement of each surface point on one axis and a position of each surface point on the other axis. In other words, each flexure display of FIG. 6 shows an interpolation line connecting measurement points similar to the flexure display 400 of FIG. 4.

In FIG. 6, the plurality of flexure displays (620a, 620b, and 620c) are based on measurement results obtained at different point in time. In the illustrated example, an equal load is applied to the same subject on three different occasions, the flexure display 620a is obtained based on a result measured on Jan. 1, 2000, the flexure display 620b is obtained based on a result measured on Mar. 1, 2000, and the flexure display 620c is obtained based on a result measured on May 1, 2000.

In addition, in FIG. 6, images of the bone (610a, 610b, and 610c) of the timings when the flexure displays are obtained are correlated to the flexure displays, respectively. The image of the bone is, for example, a cross sectional image formed by the cross sectional image formation unit (represented by reference numeral 18 in FIG. 1). Alternatively, each image of the bone may be an image based on other modalities other than the ultrasound such as a roentgen image and a CT image.

Pair images (600a, 600b, and 600c) in which the flexure display and the image of the bone at the timing when the flexure display is obtained are correlated to each other are arranged in a time sequential order. In other words, the pair image 600a corresponding to Jan. 1, 2000, the pair image 600b corresponding to Mar. 1, 2000, and the pair image 600c corresponding to May 1, 2000 are arranged along the horizontal direction.

As described, the display example of FIG. 6 shows a state of temporal change of the shape of the bone surface. With the display example of FIG. 6, for example, it is possible to easily visually understand the gradual union process of a fractured bone.

Figure 7:
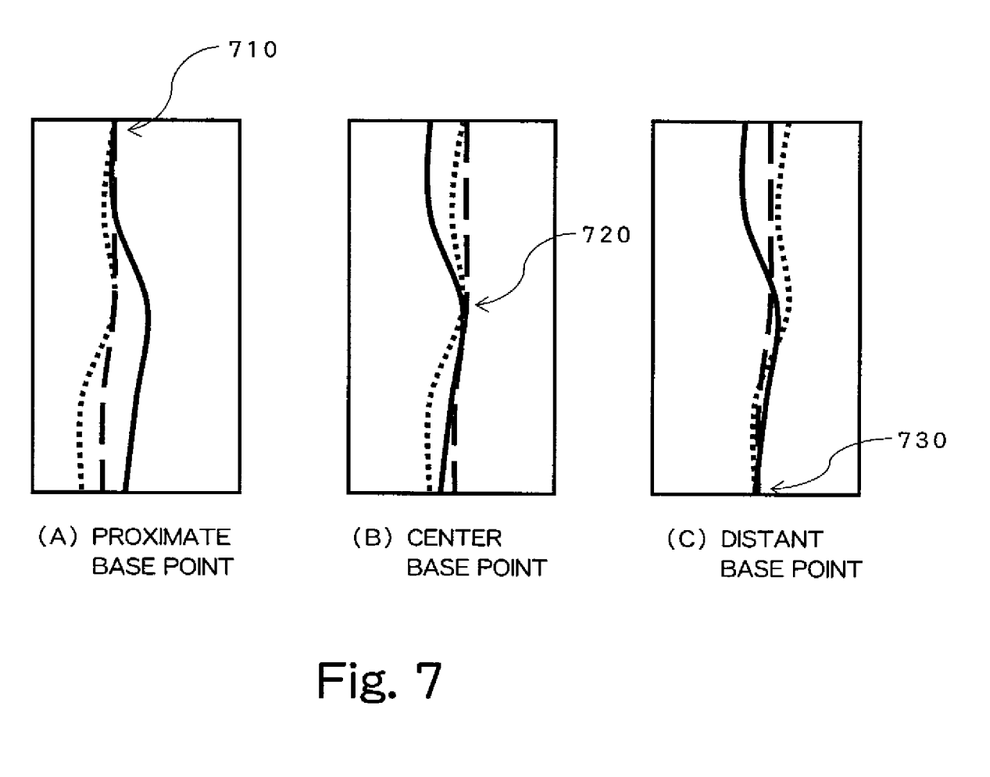
FIG. 7 is a diagram for explaining a fourth display example of a measurement result image.

FIG. 7 is a diagram for explaining a fourth display example of the measurement result image. The display example of FIG. 7 is a display example showing a state of temporal change of the shape of the bone surface, by overlapping a plurality of flexure curves obtained at timings which differ from each other.

FIG. 7(A) is a display example in which a plurality of flexure curves are overlapped with a base point at a proximate portion 710 of a bone. In FIG. 7(A), three different curves shown with dotted and solid lines show the flexure curves obtained at different points in time. For example, flexure curves are extracted from flexure displays (620a, 620b, and 620c) of three different timings shown in FIG. 6, and the extracted flexure curves of three timings are shown with dotted and solid lines in FIG. 7(A).

In FIG. 7(A), the flexure curves of three different timings are overlapped with the base point at a proximate portion 710 of the bone. In other words, the flexure curves of three different timings are overlapped with a base point at an uppermost portion of the flexure curves (for example, a position of the beam number 1 in FIG. 2).

FIG. 7(B) is a display example in which a plurality of flexure curves are overlapped with a base point at a center portion 720 of the bone. In FIG. 7(B) also, three different curves shown with dotted and solid lines are flexure curves obtained at timings which differ from each other. In FIG. 7(B), the flexure curves of three different timings are overlapped with a based point at the center portion 720 of the bone. In other words, the flexure curves of three different timings are overlapped with a base point at a center portion of the flexure curves (for example, a position of the beam number 3 in FIG. 2).

FIG. 7(C) is a display example in which a plurality of flexure curves are overlapped with a base point at a distant portion 730 of the bone. In FIG. 7(C) also, three different curves shown with dotted and solid lines are flexure curves obtained at timings which differ from each other. In FIG. 7(C), the flexure curves at three different timings are overlapped with a base point at a distant portion 730 of the bone. In other words, the flexure curves of three different timings are overlapped with a base point at a lowermost portion of the flexure curves (for example, a position of beam number 5 in FIG. 2).

As described, each of the display examples shown in FIG. 7 shows a state of temporal change of the shape of the bone surface by overlapping a plurality of flexure curves obtained at different timings. With the display example of FIG. 7, for example, it is possible to easily visually understand the change of the shape of the bone surface in the gradual union process of a fractured bone.

A preferred embodiment of the present invention has been described. The above-described embodiment has the following advantages. For example, with the display forms of FIGS. 4-7, it is possible to easily imagine a deformation of a bone with respect to a load, and these display forms become valuable information for understanding a state of a stress experienced by the bone with respect to the load. In addition, it is possible to quickly discover a measurement error due to, for example, movement of the body of the subject and an alignment error of a sensor, and, thus, a highly precise evaluation can be achieved. By showing the display forms of FIGS. 4-7 to the subject, it is possible to explain the measurement result to the subject in a manner understandable for the subject.

Although the preferred embodiments of the present invention have been described using specific terms, such description is for illustrative purposes only, and it is to be understood that modifications and variations may be made without departing from the spirit or scope of the appended claims. For example, it is possible to employ an embodiment in which a program is created for realizing constituting elements such as the echo tracking processor unit 20, the shape measurement unit 22, the measurement data generator unit 24, the data storage 26, and the display image formation unit 32 of FIG. 1 and a computer may be operated with the program so that the computer functions as the image formation device which forms a display image shown in FIGS. 4-7. The display images of FIGS. 4-7 are not limited to those displayed on the display 34 and may be, for example, printed on paper.

What is claimed is:

1. An ultrasound diagnosis apparatus comprising:
   a computer programmed to cause the computer to operate as:
   a surface detector unit configured to receive a plurality of echo signals and to detect a plurality of surface points corresponding to a surface of the bone based on a plurality of echo signals;
   a shape measurement unit configured to measure a quantity indicating a shape of the surface of the bone when a load is applied to the bone based on the plurality of detected surface points; and
   a display image formation unit configured to form a measurement result image in which the measured quantity, an amount of load applied to the bone, and a time when the load is applied to the bone are correlated with each other; and
   a display configured to display the measurement result image,
   wherein the display image formation unit is configured to form, as the measurement result image, a characteristic curve graph which shows the measured quantity on one axis and the amount of load on the other axis, and to form a time marker corresponding to a time which is set using a user interface for time setting on a characteristic curve, in the characteristic curve graph, in which the measured quantity and the amount of the load are correlated.

2. The ultrasound diagnosis apparatus according to claim 1, wherein
   the shape measurement unit is configured to measure an amount of displacement of the surface of the bone by measuring the amount of displacement of each of the plurality of detected surface points before and after the application of the load to the bone; and
   the display image formation unit is configured to form the measurement result image of the amount of load applied to the bone as a load graph in which time and the amount of load are correlated by showing the time on one axis and the amount of load on the other axis, the load graph including a time marker indicating the time set by the user interface for time setting, and
   the display image formation unit is configured to form the measurement result image of the measured amount of displacement of the bone surface as a displacement graph in which positions of the plurality of detected surface points and the amount of displacement of the surface points are correlated by showing the amount of displacement of the surface points on one axis and the position of the surface points on the other axis, and
   the amount of displacement of the surface points of the displacement graph corresponds to the amount of load applied to the bone at the time corresponding to the time marker.

3. The ultrasound diagnosis apparatus according to claim 2, wherein
   the display image formation unit is configured to form the measurement result image of a measured amount of strain of the bone when the load is applied as a strain graph in which time and the amount of strain are correlated by showing the time on one axis and the amount of strain on the other axis.

4. The ultrasound diagnosis apparatus according to claim 1, wherein
   the display image formation unit is configured to form, as the measurement result image, the characteristic curve graph showing a measured amount of displacement on one axis and the amount of load applied to the bone on the other axis the characteristic curve graph including a time marker which corresponds to a point on the characteristic curve in the characteristic curve graph corresponding to the amount of displacement and the amount of load at the time set by the user interface for time setting.

5. An ultrasound diagnosis apparatus comprising:
a computer programmed to cause the computer to operate as:
  a surface detector unit configured to receive a plurality of echo signals and to detect a plurality of surface points corresponding to a surface of the bone based on a plurality of echo signals;
  a shape measurement unit configured to measure a quantity indicating a shape of the surface of the bone, an amount of displacement of each of the plurality of surface points before and after application of a load to the bone, based on the plurality of detected surface points; and
  an image formation unit configured to form a displacement graph in which positions of the plurality of surface points and amounts of displacement are correlated by showing the amount of displacement at each surface point on one axis and a position of each surface point on the other axis, wherein
  the image formation unit is configured to form a measurement result image showing a plurality of displacement graphs obtained by applying an equal load to the bone at timings which differ from each other to show a state of temporal change of a shape of the bone surface, to form a characteristic curve graph which shows the amount of displacement on one axis and an amount of load on the other axis, and to form a time marker corresponding to a specific time on a characteristic curve, in the characteristic curve graph, in which the amount of displacement and the amount of load are correlated.

6. The ultrasound diagnosis apparatus according to claim 5, wherein
the image formation unit is configured to form a pair image in which each displacement graph and an image of a bone at a timing when the displacement graph is obtained are correlated to each other, and is configured to form the measurement result image by arranging a plurality of pair images obtained at timings which differ from each other.

7. The ultrasound diagnosis apparatus according to claim 5, wherein
the image formation unit is configured to form the measurement result image by setting a base point corresponding to a same position on the bone surface for each of the plurality of displacement graphs obtained at different timings and overlapping each of the plurality of displacement graphs at the respective base points of the plurality of displacement graphs.

8. A method of displaying a measurement result, comprising the steps of:
  detecting a plurality of surface points of a bone surface by transmitting and receiving ultrasound generated by an ultrasound diagnostic apparatus to and from a bone;
  measuring a quantity indicating a shape of the bone surface when a load is applied to the bone based on the plurality of surface points detected from the bone surface;
  setting, using a user interface for time setting, a time when the load is applied to the bone;
  displaying a first measurement result image in which the measured quantity, an amount of load, and a time when the load is applied to the bone are correlated with each other, wherein the displaying the first measurement result image includes displaying a characteristic curve graph which shows the measured quantity on one axis and the amount of load on the other axis, and displaying a time marker corresponding to a time set using the user interface for time setting on a characteristic curve, in the characteristic curve graph, in which the measured quantity and the amount of load are correlated.

9. The method of displaying measurement result according to claim 8, wherein
  an amount of displacement for each surface point before and after the application of the load to the bone is measured as the measured quantity; and
  a load graph in which the time and the amount of load are correlated by showing the time on one axis and the amount of load on the other axis and a displacement graph in which positions of a plurality of surface points and the amounts of displacement are correlated by showing the amount of displacement of each surface point on one axis and a position of each surface point on the other axis are formed as the first measurement result image, and the amount of displacement corresponding to the amount of load of the time corresponding to a time marker displayed in the load graph is displayed in the displacement graph.

10. The method of displaying measurement result according to claim 9, wherein
  the displaying the first measurement result image includes displaying a strain graph in which the time and an amount of strain are correlated by showing the time on one axis and the amount of strain on the other axis.

11. The method of displaying measurement result according to claim 10, wherein
  the setting the time when the load is applied to the bone includes forming and displaying a time setting bar for setting time and setting the time when the load is applied to the bone using the time setting bar, and
  the displaying of the first measurement result image includes displaying a time marker in the load graph and the strain graph according to the time which is set through the time setting bar.

12. The method of displaying measurement result according to claim 8, wherein
  the setting the time when the load is applied to the bone includes forming and displaying a time setting bar for setting time, and the time marker is displayed in the characteristic curve graph according to the time which is set through the time setting bar.

13. The method of displaying measurement result according to claim 8, wherein
  the measuring includes measuring an amount of displacement in each surface point before and after the application of the load to the bone; the method further comprising
  forming a displacement graph in which positions of a plurality of surface points and the amounts of displacement are correlated by showing the amount of displacement of each surface point on one axis and the position of each surface point on the other axis; and
  displaying a second measurement result image showing a state of temporal change of a shape of the bone surface based on a plurality of displacement graphs obtained at timings which differ from each other.

14. The method of displaying measurement result according to claim 13, wherein
the second measurement result image is formed by forming a pair image in which each displacement graph and an image of the bone at the timing when the displacement graph is obtained are correlated and arranging a plurality of pair images obtained at timings which differ from each other.

15. The method of displaying the measurement result according to claim 13, wherein the second measurement result image is formed by setting, for each of the plurality of displacement graphs obtained at different timings, a base point which corresponds to a same position on the bone surface and overlapping the base points of the plurality of displacement graphs.

\* \* \* \* \*